United States Patent
Stock et al.

(10) Patent No.: US 9,414,593 B2
(45) Date of Patent: Aug. 16, 2016

(54) HERBICIDAL COMPOSITIONS

(75) Inventors: David Stock, Bracknell (GB); Philip Taylor, Bracknell (GB); Rudolf Schneider, Muenchwilen (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 1111 days.

(21) Appl. No.: 12/447,269

(22) PCT Filed: Oct. 25, 2007

(86) PCT No.: PCT/EP2007/009276
§ 371 (c)(1),
(2), (4) Date: Jan. 14, 2011

(87) PCT Pub. No.: WO2008/049618
PCT Pub. Date: May 2, 2008

(65) Prior Publication Data
US 2011/0098178 A1    Apr. 28, 2011

(30) Foreign Application Priority Data

Oct. 27, 2006  (GB) .................................. 0621440.7

(51) Int. Cl.
*A01N 43/40*    (2006.01)
*A01N 43/90*    (2006.01)

(52) U.S. Cl.
CPC ................ *A01N 43/40* (2013.01); *A01N 43/90* (2013.01)

(58) Field of Classification Search
CPC ... A01N 43/90; A01N 2300/00; A01N 25/30; A01N 57/20; A01N 43/40; A01N 25/32
USPC ........................................................ 504/103
See application file for complete search history.

(56) References Cited

U.S. PATENT DOCUMENTS

| | | | |
|---|---|---|---|
| 2002/0006889 A1* | 1/2002 | Wurtz et al. ................... | 510/421 |
| 2005/0038094 A1* | 2/2005 | Warrington ................... | 514/383 |
| 2005/0096226 A1* | 5/2005 | Stock et al. ................... | 504/141 |
| 2007/0275854 A1* | 11/2007 | Hess et al. .................... | 504/128 |

FOREIGN PATENT DOCUMENTS

| | | |
|---|---|---|
| EP | 0579052 | 1/1994 |
| EP | 0655197 | 5/1995 |
| EP | 1062217 | 6/2003 |
| EP | 1018299 | 3/2005 |
| RU | 2337545 | 11/2008 |
| WO | 93/04585 | 3/1993 |
| WO | 94/18837 | 9/1994 |
| WO | 9418837 | 9/1994 |
| WO | 96/22020 | 7/1996 |
| WO | 98/00021 | 1/1998 |
| WO | 99/47525 | 9/1999 |
| WO | 00/56146 | 9/2000 |
| WO | 0056146 | 9/2000 |
| WO | WO 0056146 A1 * | 9/2000 |
| WO | 01/17351 | 3/2001 |
| WO | 01/17352 | 3/2001 |
| WO | 01/17353 | 3/2001 |
| WO | 01/17972 | 3/2001 |
| WO | 0147356 | 7/2001 |
| WO | 02/102153 | 12/2002 |
| WO | 03/028466 | 4/2003 |
| WO | 01/47356 | 7/2003 |
| WO | 03/099012 | 12/2003 |
| WO | 03/105588 | 12/2003 |
| WO | 03/105589 | 12/2003 |
| WO | 2006/034817 | 4/2006 |
| WO | 2006034817 | 4/2006 |
| WO | WO 2006034817 A2 * | 4/2006 |
| WO | 2006/061562 | 6/2006 |
| WO | 2007/073933 | 7/2007 |
| WO | 2008/092615 | 8/2008 |

OTHER PUBLICATIONS

Forster and Porter, Pinoxaden—A new postemergence graminicide for wheat and barley, North Central Weed Science Proceedings 60:209 (2005).*
Syngenta Topik 240 EC 2005 Label downloaded from the website http://fluoridealert.org/wp-content/pesticides/msd/clodinafop-p.topik.240.sc.pdf on Feb. 26, 2015.*
Solvesso 150 label [downloaded from the website https://www.exxonmobilchemical.com/Chem-English/Files/Resources/aromatic-150-product-safety-summary.pdf on Feb. 26, 2015].*
Brzezinski et al., J Phys Chem 101: 5607 (1997).*
Australian Pesticide Authority, 2005 at pp. 24 and 11. [Downloaded from the website http://archive.apvma.gov.au/registration/assessment/docs/prs_pinoxaden.pdf on Feb. 26, 2015].*
Database CAPLUS [Online], Chemical Abstracts Service, Columbus, Ohio, US; Tris(2-ethylhexyl) phosphate: exemption from the requirement of a tolerance; XP002510628, retrieved from STN Database accession No. 2007.269877 abstract & Federal Register, 72(25), 5621-5624, Feb. 7, 2007.
U. Hofer, M. Muehlebach et al. "Pinoxaden—for broad spectrum grass weed management in cereal crops", Journal of Plant Diseases and Protection, Special Issue XX (Sonderheft XX), 2006, pp. 989-995.
C.A. Ruchs et al., "AXIAL, a cereal selective graminicide for the control of annual ryegrass (Lolium rigidum Gaudin) and other major grass weeds", Fifteenth Australian Weeds Conference, 2006, pp. 838-841.
M. Muehlebach et al., "Discovery and SAR of Pinoxaden: a new broad spectrum, postemergence cereal herbicide", in "Pesticide Chemistry, Crop Protection, Public Health, Environmental Safety", ed. H. Ohkawa, H. Miyagawa and P.W. Lee, Wiley, Weinheim, 2007, pp. 101-110.

(Continued)

Primary Examiner — Sue Liu
Assistant Examiner — Thor Nielsen
(74) Attorney, Agent, or Firm — R. Kody Jones

(57) ABSTRACT

A liquid herbicidal composition containing pinoxaden and an adjuvant, where the adjuvant is a built-in adjuvant consisting of a trisester of phosphoric acid with aliphatic or aromatic alcohols and/or a bis-ester of alkyl phosphonic acids with aliphatic or aromatic alcohols.

18 Claims, No Drawings

(56) References Cited

OTHER PUBLICATIONS

J. Wenger and T. Niderman, "Acetyl-CoA Carboxylase Inhibitors", Chapter 9 of "Modern Crop Protection Compounds", ed. W. Kramer and U. Schirmer, Wiley, Weinheim, 2007, pp. 335-357.

"A World Compendium—The Pesticide Manual", 14th edition, 2006, ed. C.D.S. Tomlin, British Crop Production Council, entry 668 "pinoxaden" (pp. 843-844).

"A World Compendium—The Pesticide Manual", 14th edition, 2006, ed. C.D.S. Tomlin, British Crop Production Council, entry 160 "clodinafop-propargyl" (pp. 199-200) and entry 832 "tralkoxydim" (pp. 1048-1049).

"A World Compendium—The Pesticide Manual", 12th edition, 2000, ed. C.D.S. Tomlin, British Crop Production Council, entry 156—"clodinafop-propargyl" (pp. 186-187) and entry 767 "tralkoxydim" (pp. 914-915).

"A World Compendium—The Pesticide Manual", 14th edition, 2006, ed. C.D.S. Tomlin, British Crop Production Council, entry 370 "florasulam" (pp. 470-471) and entry 839 "triasulfuron" (pp. 1057-1058).

"A World Compendium—The Pesticide Manual", 12th edition, 2000, ed. C.D.S. Tomlin, British Crop Production Council, entry 351 "florasulam" (pp. 420-421) and entry 773 "triasulfuron" (pp. 922-923).

"A World Compendium—The Pesticide Manual", 14th edition, 2006, ed. C.D.S. Tomlin, British Crop Production Council, entry 166 "cloquintocet-mexyl" (pp. 207-208), entry 524 "mefenpyr-diethyl" (p. 666) and entry 494 "isoxadifen-ethyl" (p. 627).

"A World Compendium—The Pesticide Manual", 12th edition, 2000, ed. C.D.S. Tomlin, British Crop Production Council, entry 163 "cloquintocet-mexyl" (pp. 195-196) and entry 492 "mefenpyr-diethyl" (p. 594-595).

Ukrainian Decision to Grant; UA a200809541, Oct. 27, 2008.

Environmental Protection Agency—Tris (2-ethylhexyl) Phosphate; Exemption from the Requirement of a Tolerance, Federal Register vol. 72, No. 25, Feb. 7, 2007, pp. 5621-5624.

* cited by examiner

HERBICIDAL COMPOSITIONS

This application is a 371 of International Application No. PCT/EP2007/009276 filed Oct. 25, 2007, which claims priority to GB 0621440.7 filed Oct. 27, 2006, the contents of which are incorporated herein by reference.

The present invention relates to herbicidal compositions which contain organic phosphates or phosphonates as adjuvants.

It is known within the literature that phosphate and phosphonate materials have activity-enhancing properties when used in combination with pesticidal active ingredients. For example, WO9800021 teaches that phosphonates are effective at enhancing fungicidal activity. EP1018299 teaches that phosphate materials can act as "accelerator adjuvants" in facilitating enhanced cuticle penetration of the target leaf by herbicides. According to WO00056146 phosphate and phosphonate materials are used to enhance the physical stability of herbicidal compositions in controlling the crystallization of the herbicide.

Many grass herbicides (graminicides) for cereals require an adjuvant to develop full biological activity. In many cases the physico-chemical properties of the active ingredients make it difficult to add an adjuvant to the composition. Either because the chemical or physical stability of the active ingredient suffers from the added adjuvant or because biological performance is insufficient. It is in particular very challenging to make a biologically efficient and stable composition due to the chemical and physical instability of the herbicides used.

It has now been found that a composition of the herbicide pinoxaden shows excellent biological efficacy and chemical and physical stability when tris-esters of phosphoric acid and/or bis-esters of alkyl phosphonic acids with aliphatic or aromatic alcohols are used as adjuvants.

As a rule, the adjuvants may be added to the spray tank (so-called tank-mix adjuvants) or may be incorporated into the herbicide composition (so-called built-in adjuvants).

It has also been found that the built-in level of the said type of adjuvant system allows the development of stable compositions of pinoxaden containing a sufficient amount of the phosphate adjuvant in a one-pack concept (built-in) that does not require the use of a separate tank-mix adjuvant by the end user to boost activity, and realise the full biological potential of the dose of herbicide applied per unit crop area.

Graminicidal herbicides applied in a post-emergence treatment in cereals typically benefit from the use of an oil-type adjuvant to enhance activity under field conditions. Oil-type adjuvants are typically used at 0.5% of the final spray volume. For a 200 l/ha spray application, this equates to 1 l per hectare of oil-type adjuvant. This amount of tank-mix oil would represent a significant burden to build into a user-acceptable one-pack formulated product, due to the practical volume limitation of the product. In addition, building in such an amount of oil presents significant chemical and physical stability issues.

Conventional tank-mix adjuvant oils available on the marketplace are typically composed of 3 categories of oil: mineral oil, seed-oil and methylated seed oil. Such oils typically have a low degree of solvency power, so cannot be built into most compositions with typical solvents known to those skilled in the art, in particular into EC's, without resulting in crystallisation of the active ingredient out of solution. Such oils can only be used with active ingredients which are also oils at room temperature, or which are relatively easy to dissolve due to a low melting point.

For a conventional composition of pinoxaden, such as an EC, it is not chemically and physically possible to incorporate sufficient conventional oil-type adjuvant into a one-pack (built-in) composition. In order to achieve sufficient activity under field conditions, a 0.5% level of an adjuvant blend is needed containing methylated seed oil, co-solvent and specific combination of surfactant co-adjuvants which also act as emulsifiers. Extensive testing of a range of chemical types of adjuvant has shown that such materials cause chemical instability issues with pinoxaden, which result in insufficient stability according to regulatory accepted standards. In addition, the potency of conventional adjuvant chemistry is insufficient to build them into a one-pack product irrespective of chemical and physical stability issues.

Thus, it has been found that said tris-esters of phosphoric acid with aliphatic or aromatic alcohols and/or bis-esters of alkyl phosphonic acids with aliphatic or aromatic alcohols are a high performance oil-type adjuvant which has allowed a chemically and physically stable, active one-pack composition to be developed. Such built-in compositions are preferred by farmers because a tank-mix adjuvant is not required. This results in easier handling, especially in markets where products are sold in bulk. It may also lead to significant cost savings in manufacture because production and packaging of a separate tank-mix adjuvant is not required any more.

It has also been found that the new compositions with built-in adjuvants, in particular in the form of an EC, match or even exceed the efficacy of corresponding conventional compositions with a tank-mix adjuvant.

The present invention therefore provides a liquid herbicidal composition containing pinoxaden and an adjuvant, where the adjuvant is a built-in adjuvant consisting of a tris-ester of phosphoric acid with aliphatic or aromatic alcohols and/or a bis-ester of alkyl phosphonic acids.

Pinoxaden is the 8-(2,6-diethyl-p-tolyl)-1,2,4,5-tetrahydro-7-oxo-7H-pyrazolo[1,2-d][1,4,5]oxadiazepin-9-yl-2,2-dimethylpropionate and also the acid form thereof which have been described, for example, as compounds no. 1.007 and 1.008 in EP1062217.

The tris-esters of phosphoric acid with aliphatic or aromatic alcohols and/or bis-esters of alkyl phosphonic acids which are useful in the new composition have been described, for example, in WO0147356, WO0056146, EP-A-0579052 or EP-A-1018299 or are commercially available under their chemical name. Preferred tris-esters of phosphoric acid for use in the new compositions are tris-(2-ethylhexyl)phosphate, tris-n-octyl phosphate and tris-butoxyethyl phosphate, where tris-(2-ethylhexyl)phosphate is most preferred. Suitable bis-ester of alkyl phosphonic acids are bis-(2-ethylhexyl)-(2-ethylhexyl)-phosphonate, bis-(2-ethylhexyl)-(n-octyl)-phosphonate, dibutyl-butyl phosphonate and bis(2-ethylhexyl)-tripropylene-phosphonate, where bis-(2-ethylhexyl)-(n-octyl)-phosphonate is particularly preferred.

The compositions according to the present invention are biologically highly effective and chemically and physically stable. Preferably, the compositions are characterized by a breakdown of less than 2.5% pinoxaden after 2 weeks storage at a temperature of 50° C.

A preferred composition according to the present invention contains
0.5-50% pinoxaden, preferably 2-20%, most preferably 5-10%;
2-80% adjuvant, preferably 10-60%, most preferably 15-40%;
0.5-50% emulsifiers, preferably 2-30%, more preferably 2-10%,
0-90% solvents, preferably 10-60%, more preferably 15-40%, 0-80% water and 0-80% oil carrier (different from the adjuvant or solvent carrier).

The emulsifiers useful in the new compositions are known in the art and comprise, for example, salts of alkyl sulfates, such as diethanolammonium lauryl sulfate; salts of arylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981. It is also possible to use a mixture of one or more of these emulsifiers.

Preferred solvents which are suitable for use in the new compositions are heavy aromatic hydrocarbon blends and one or more alcohols or derivatives of said alcohols selected from the group consisting of 2-ethylhexanol, n-octanol, tetrahydrofurfurylalkohol, 2-methyl-2,4-pentanediol, 4-hydroxy-4-methyl-2-pentanon, lactic acid methylester, lactic acid butylester, cyclohexanol, benzyl alcohol, benzyl benzoate, benzyl lactate, N-methylpyrrolidone, gamma-butyrolactone and dimethylsulfoxide, where tetrahydrofurfurylalkohol, benzyl alcohol and 2-methyl-2,4-pentanediol and particularly tetrahydro-furfurylalkohol is preferred, a mixture of one or more of these materials.

The new compositions can comprise additional formulation aids known in the art such as crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micron utrients, plasticisers, glidants, lubricants, dispersants, thickeners, antifreezes, microbiocides, and also liquid and solid fertilisers.

The composition according to the present invention may contain a safener. Preferably, the safener is selected from the group consisting of cloquintocet-mexyl, mefenpyr-diethyl, cyprosulfamid and isoxadifen-ethyl. These safeners are known and are described, for example, in The Pesticide Manual, Twelfth Edition, British Crop Protection Council, 2000 or other readily available resources.

Optionally, a co-herbicide for pinoxaden can be incorporated into the compositions according to the present invention. It is preferred to select the co-herbicide from the group consisting of aryloxy- and heteroaryloxyphenoxy propionic acids, cyclohexandiones, sulfonyl urea, triazolopyrimidines, nitriles, thiocarbamates, dinitroanilines, benzoic acids, phenoxy acids and pyridine carboxylic acids. Of particular interest are clodinafop, fenoxaprop, tralkoxydim, prosulfocarb, triasulfuron, prosulfuron, amidosulfuron, iodosulfuron, chlorsulfuron, flupyrsulfuron, mesosulfuron, metsulfuron, sulfosulfuron, thifensulfuron, tribenuron, tritosulfuron, florasulam, metosulam, flumetsulam, pyroxsulam, 2,4-D, 2,4-DP, dichlorprop-p, MCPA, mecoprop, mecoprop-p, MCPB, clopyralid, bromoxynil, bromoxynil-octanoate, ioxynil, ioxynil-octanoate, fluoroxypyr, trifluralin, diflufenican, picolinafen, pendimethalin and triallate, where tralkoxydim, triasulfuron, diflufenican, florasulam, pyroxsulam, pyroxsulam in combination with cloquintocet, clodinafop and clodinafop in combination with cloquintocet are preferred.

Preferably, the compositions according to the present invention are prepared in the form of an emulsion concentrate (EC), oil dispersion (OD), dispersible concentrate (DC), suspo-emulsion (SE) or emulsion in water (EW), but it is also possible that the emulsions are present in the form of gels, wettable powders, water-dispersible granules, water-dispersible tablets, effervescent compressed tablets, microemulsifiable concentrates, oil-in-water emulsions, oil flowables, aqueous dispersions, capsule suspensions, emulsifiable granules, or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient (i.e. pinoxaden, optionally in combination with a co-herbicide and/or a safener) with formulation adjuvants and other co-formulants in order to obtain compositions in the form of solutions, dispersions or emulsions. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine matrix particles to be formed wherein the active ingredient is present in the form of finely divided particles in a solid matrix of a base substance, but in that case the matrix particle is not encapsulated.

The invention relates also to a method for inhibiting or controlling undesirable plant growth, wherein a herbicidally effective amount of the composition according to the present invention is applied to the plants or their habitat.

Crops of useful plants in which the compositions according to the invention can be used include especially cereals, in particular wheat, durum wheat, triticale, rye and barley. The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Apera, Avena, Setaria, Sinapis, Lolium, Echinochloa, Bromus, Alopecurus, Phalaris, Amaranthus, Chenopodium, Convolvulus, Chrysanthemum, Papaver, Cirsium, Polygonum, Matricaria, Galium, Viola* and *Veronica*.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33BC (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The following Examples illustrate the invention further but do not limit the invention.

EXAMPLE 1

Sample Formulation Compositions (% w/v)

The use of tris-(2-ethylhexyl)phosphate as a high performance oil-type adjuvant has allowed a chemically stable, active one-pack formulation to be developed. The stability of typical compositions according to the present invention, compositions A and B, in form of EC's are outlined below in comparison with other built-in adjuvant compositions in the following Table 1.

TABLE 1

| Composition | A | B | C | D | E | F |
|---|---|---|---|---|---|---|
| Pinoxaden (herbicide) | 5 | 6.9 | 6.9 | 4.6 | 4.6 | 4.6 |
| Cloquitocet mexyl (Safener) | 1.25 | 1.725 | 1.725 | 1.15 | 1.15 | 1.15 |
| Castor oil ethoxylate (30 EO) (Emulsifier) | 5 | 5 | | | | |
| Castor oil ethoxylate (20 EO) (Emulsifier) | | | | | 30 | 20 |
| Ethoxylated isostearyl alcohol (Emulsifier) | | | 20 | | | |
| Ethoxylated tristyrylphenol (10 EO) (Emulsifier) | | | | | | 12 |
| Alkylbenzene sulfonate calcium salt (Emulsifier) | 2 | 2 | | | 0.5 | 0.5 |
| Isopropyl myristate (Adjuvant) | | | | | 30 | |
| Rape seed oil methyl ester (Adjuvant) | | | 27.2 | | | 40 |
| Isoparafinic hydrocarbon (Adjuvant) | | | | 10 | | |
| Tris-(2-ethylhexyl) phosphate (Adjuvant) | 34 | 32 | | | | |
| Tetrahydrofurfuryl alcohol (Solvent) | 18 | 18 | 20 | 15 | 15 | 20 |
| Mixture aromatic hydrocarbons (Solvent) | Up to 100 | Up to 100 | Up to 100 | Up to 100 | Up to 100 | Up to 100 |
| % Pinoxaden breakdown after 2 weeks at 50° C. | −2.0 | −2.0 | −12.4 | −25.7 | −22.1 | −20.8 |

Compositions A and B according to the present invention containing the built-in tris-(2-ethylhexyl)phosphate show enhanced stability of pinoxaden in comparison to the other formulation systems. Further, compositions A and B contain a sufficient quantity of phosphate adjuvant that use of an additional tank-mix adjuvant is not required.

Compositions C and F (EC's) shows a composition containing built-in rapeseed oil methyl ester. This shows excessive breakdown under storage stability testing, and furthermore does not contain sufficient methylated oil material to express the full biological potential of pinoxaden under field conditions. Similarly composition D (an EC) contains an isoparaffinic hydrocarbon known as an adjuvant material in tank-mix products such as Agridex adjuvant and Penetrator adjuvant, shows a high level of breakdown of pinoxaden. Mineral oil based products are additionally known from EP1062217 and they have been found to be much less effective than tris-(2-ethylhexyl)phosphate at enhancing pinoxaden activity.

In WO9622020, various ester derivatives, in addition to methylated seed oils have been shown to have activity enhancing effects with a range of active ingredients. Within composition E (an EC) the incorporation of isopropyl myristate was investigated, and again this has shown unacceptable breakdown of pinoxaden.

EXAMPLE 2

Sample Formulation Compositions (% w/v)

The examples of Table 2 show that stable compositions with tris-(2-ethylhexyl)phosphate as a high performance adjuvant according to the invention are obtained also in the presence of florasulam and/or clodinafop as co-herbicide.

TABLE 2

| Composition | G | H | I |
|---|---|---|---|
| Pinoxaden (herbicide) | 2.5 | 4.5 | 3 |
| Cloquintocet mexyl (Safener) | 0.625 | 1.125 | 0.75 |
| Clodinafop (co-herbicide) | 2.5 | | 3 |
| Florasulam (co-herbicide) | | 0.5 | 0.75 |
| Alkylbenzene sulfonate calcium salt (Emulsifier) | 2 | 2 | 2 |
| Castor oil ethoxylate (30EO) (Emulsifier) | 5 | 5 | 5 |
| Tris-(2-ethylhexyl) phosphate (Adjuvant) | 34 | 34 | 34 |
| Tetrahydrofurfuryl alcohol (Solvent) | 18 | 18 | 18 |
| Mixture aromatic hydrocarbons (Solvent) | Up to 100 | Up to 100 | Up to 100 |
| % Pinoxaden breakdown after 2 weeks at 50° C. | ~2 | ~2 | ~2 |

EXAMPLE 3

Comparison of (1) a 5% EC formulation of pinoxaden according to the present invention with 34% of tris-(2-ethylhexyl) phosphate as an in-built adjuvant, with (2) a 10% EC formulation of pinoxaden without built-in adjuvant together with the rapeseed oil methyl ester adjuvant as a tank-mix adjuvant at 0.5% of the spray volume.

EC (1) corresponds to composition A according to Table 1; EC (2) is the commercially available product Axial 100EC herbicide.

The test plants were sprayed with 30 g/ha pinoxaden using a 200 l/ha spray volume. The results obtained by visual assessment 21 days after the spray application are summarized in the following Table 3. It should be noted that whilst the treatment with EC (2) applies 1 L of the rapeseed oil methyl ester adjuvant as a tank-mix adjuvant per 200 L spray solution, the treatment with EC (1) results from the application of only 600 ml of composition A from Table 1, and this composition in turn is only 34% tris-(2-ethylhexyl) phosphate built-in adjuvant.

TABLE 3

| | Control of weeds (%) | | | | |
|---|---|---|---|---|---|
| | Alopecurus | Apera | Avena | Lolium | Phalaris |
| EC (1) | 79 | 98 | 90 | 81 | 89 |
| EC (2) | 67 | 92 | 89 | 80 | 90 |

These data illustrate that the phosphate-containing EC (1) of pinoxaden according to the present invention matches or even exceeds the activity of the conventional EC (2) with the tank-mix adjuvant, despite the presence of much less phosphate adjuvant within the spray tank.

EXAMPLE 4

Comparison of biological efficacy of EC (1) containing Tris-(2-ethylhexyl)phosphate according to the invention and EC (3) containing conventional methylated rape seed oil as adjuvant. EC (1) corresponds to composition A according to Table 1; EC (3) corresponds to composition F in Table 1.

The test plants were treated in the greenhouse with 1, 2, 4, and 8 g/ha pinoxaden using the formulations EC (1) and EC (3). After assessment of the injury 20 days after treatment ED (90) values were calculated. The ED (90) value is the rate of pinoxaden which is required to achieve 90% efficacy. Table 4 shows clearly that with EC (1) significantly lower rates are required.

TABLE 4

| | Control of weeds | | |
|---|---|---|---|
| | ED(90) values in g a.i/ha | | |
| Formulation | Wild oat | Italian ryegrass | Green Foxtail |
| EC (1) | 4.0 | 1.7 | 3.7 |
| EC (3) | 5.9 | 4.2 | 4.6 |

The invention claimed is:

1. A liquid herbicidal composition comprising pinoxaden and an adjuvant, wherein the adjuvant is a built-in adjuvant consisting of tris-(2-ethylhexyl) phosphate present at 15-40% of the composition, wherein the percentage of pinoxaden breakdown is less than 2.5% after 2 weeks storage at a temperature of 50° C.

2. A composition according to claim 1, which contains
   0.5-50% pinoxaden,
   5-40% of the tris-(2-ethylhexyl) phosphate adjuvant,
   0.5-50% emulsifiers,
   10-90% solvent,
   0-80% water, and
   0-80% oil, wherein the oil is different from the adjuvant and the solvent.

3. A composition according to claim 2, wherein the emulsifier is a salt of an alkyl sulphate, a salt of an arylsulfonate, an alkylphenol-alkylene oxide addition product, an alcohol-alkylene oxide addition product, a soap, a salt of an alkyl-naphthalenesulfonate, a dialkyl ester of a sulfosuccinate salt, a sorbitol ester, a quaternary amine, or a polyethylene glycol ester of a fatty acid, or a combination of one or more of these materials.

4. A composition according to claim 2, wherein the solvent includes at least one of: a heavy aromatic hydrocarbon blend; or an alcohol or a derivative thereof selected from the group consisting of 2-ethylhexanol, n-octanol, tetrahydrofurfuryl alcohol, 2-methyl-2,4-pentanediol, 4-hydroxy-4-methyl-2-pentanone, lactic acid methyl ester, lactic acid butyl ester, cyclohexanol, benzyl alcohol, benzyl benzoate, and benzyl lactate.

5. A composition according to claim 4, wherein the solvent is tetrahydrofurfuryl alcohol, benzyl alcohol or 2-methyl-2, 4-pentanediol.

6. A composition according to claim 5, wherein the solvent is tetrahydrofurfuryl alcohol.

7. A composition according to claim 1, which further contains a safener.

8. A composition according to claim 7, wherein the safener is selected from the group consisting of cloquintocet-mexyl, mefenpyr-diethyl and isoxadifen-ethyl.

9. A composition according to claim 1, which further contains a co-herbicide selected from the group consisiting of aryloxy- and heteroaryloxyphenoxy propionic acids, cyclohexanediones cyclohexandiones, sulfonyl ureas, triazolopyrimidines, nitriles, thiocarbamates, dinitroanilines, benzoic acids, phenoxy acids and pyridine carboxylic acids.

10. A composition according to claim 9, which contains clodinafop, tralkoxydim, prosulfocarb, triasulfuron, prosulfuron, amidosulfuron, chlorsulfuron, flupyrsulfuron, mesosulfuron, metsulfuron, sulfosulfuron, thifensulfuron, tribenuron, tritosulfuron, florasulam, metosulam, flumetsulam, pyroxsulam, 2,4-D, 2,4-DP, dichlorprop-p, MCPA, mecoprop, mecoprop-p, MCPB, clopyralid, bromoxynil, bromoxynil-octanoate, ioxynil, ioxynil-octanoate, fluroxypyr, trifluralin, diflufenican, pendimethalin or triallate.

11. A composition according to claim 10, which contains tralkoxydim, triasulfuron, florasulam, clodinafop or clodinafop in combination with cloquintocet.

12. A composition according to claim 1, which is in the form of an emulsion concentrate, oil dispersion, or dispersible concentrate.

13. A method for inhibiting or controlling undesirable plant growth, wherein a herbicidally effective amount of the composition according to claim 1 is applied to the plants or their habitat.

14. A method according to claim 13, wherein the composition is used in crops of wheat, durum wheat or barley.

15. A composition according to claim 1, which contains
2-20% pinoxaden,
15-40% of the tris-(2-ethylhexyl) phosphate adjuvant,
2-30% emulsifiers,
10-60% solvent,
0-80% water, and
0-80% oil, wherein the oil is different from the adjuvant and the solvent.

16. A composition according to claim 1, which further contains an emulsifier which comprises a salt of an alkyl sulfate, a salt of an arylsulfonate, an alkylphenol-alkylene oxide addition product, an alcohol-alkylene oxide addition product, a soap, a salt of an alkylnaphthalenesulfonate, a dialkyl ester of a sulfosuccinate salt, a sorbitol ester, a quaternary amine, a polyethylene glycol ester of a fatty acid, or a block copolymer of ethylene oxide and propylene oxide, or a mixture of one or more of these emulsifiers.

17. A composition according to claim 1, which further contains a solvent which comprises: a heavy aromatic hydrocarbon blend; or one or more alcohols or derivatives of said alcohols selected from the group consisting of 2-ethylhexanol, n-octanol, tetrahydrofurfuryl alcohol, 2-methyl-2,4-pentanediol, 4-hydroxy-4-methyl-2-pentanone, lactic acid methyl ester, lactic acid butyl ester, cyclohexanol, benzyl alcohol, benzyl benzoate and benzyl lactate.

18. A composition according to claim 17, wherein the solvent comprises tetrahydrofurfuryl alcohol, benzyl alcohol or 2-methyl-2,4-pentanediol.

\* \* \* \* \*